US009138498B2

(12) United States Patent
Biryukov

(10) Patent No.: US 9,138,498 B2
(45) Date of Patent: Sep. 22, 2015

(54) MODIFICATION OF POWDER STRUCTURE BY ELECTRIC FIELD

(75) Inventor: Sergey Biryukov, Beer Sheva (IL)

(73) Assignee: Ben-Gurion University of the Negev Research & Development Authority, Beer Sheva (IL)

( * ) Notice: Subject to any disclaimer, the term of this patent is extended or adjusted under 35 U.S.C. 154(b) by 538 days.

(21) Appl. No.: 13/563,995

(22) Filed: Aug. 1, 2012

(65) Prior Publication Data
US 2012/0299220 A1 Nov. 29, 2012

Related U.S. Application Data

(63) Continuation-in-part of application No. PCT/IL2011/000109, filed on Jan. 31, 2011.

(30) Foreign Application Priority Data

Feb. 4, 2010 (IL) ........................................ 203741

(51) Int. Cl.
*B29C 35/08* (2006.01)
*A61L 2/10* (2006.01)
*A61L 2/20* (2006.01)

(52) U.S. Cl.
CPC .. *A61L 2/10* (2013.01); *A61L 2/202* (2013.01)

(58) Field of Classification Search
CPC .......................... B02C 19/18; B02C 2019/183
See application file for complete search history.

(56) References Cited

U.S. PATENT DOCUMENTS

| | | | | |
|---|---|---|---|---|
| 6,660,227 | B2 | 12/2003 | Lopez Ordaz | |
| 6,737,029 | B2 | 5/2004 | Miller | |
| 6,984,361 | B2 | 1/2006 | Carman et al. | |
| 2003/0038032 | A1 | 2/2003 | Reel et al. | |
| 2003/0133828 | A1 | 7/2003 | Lucas et al. | |
| 2007/0234905 | A1* | 10/2007 | Bromberg | 96/54 |
| 2008/0297798 | A1 | 12/2008 | Wyssen | |
| 2010/0014067 | A1* | 1/2010 | Baxter et al. | 356/36 |

FOREIGN PATENT DOCUMENTS

| | | |
|---|---|---|
| WO | 03/057260 | 7/2003 |
| WO | 03/058202 | 7/2003 |
| WO | 2004/075609 | 9/2004 |
| WO | 2006/083967 | 10/2006 |

OTHER PUBLICATIONS

Herbert A. Pohl, "Dielectrophoresis, The behavior of neutral matter in non-uniform electric fields", Cambridge University Press, London, 1978.
W.C.Hinds, Aerosol Technology: Properties, Behavior, and Measurement of Airborne Particles, 2nd edition, Wiley-Interscience, 1999.
IPRP CH I of corresponding PCT application PCT/IL2011/000109—8 pages, mailed Aug. 7, 2012.

* cited by examiner

*Primary Examiner* — James Sanders
(74) *Attorney, Agent, or Firm* — Roach Brown McCarthy & Gruber, P.C.; Kevin D. McCarthy

(57) ABSTRACT

Provided are a method and an apparatus for modifying particle size of powders in closed items, comprising the exposure of said items to external electric field of suitable parameters. The degree of agglomeration of the particles can be increased or decreased. Applications to neutralization of harmful powders in mails, to dry agglomeration and to volatilization of powders in food industry and in pharmacology are described.

24 Claims, 2 Drawing Sheets

MODIFICATION OF POWDER STRUCTURE BY ELECTRIC FIELD

REFERENCE TO CO-PENDING APPLICATIONS

Figure 1A:
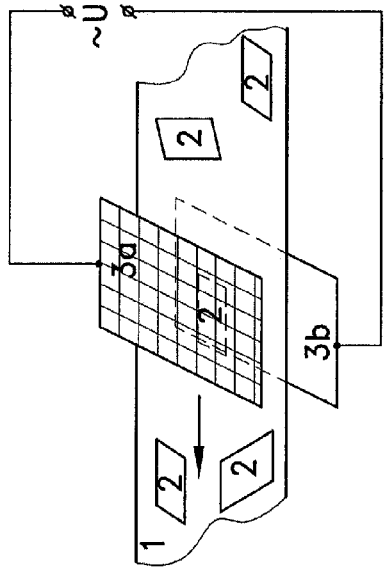
Figure 1B:
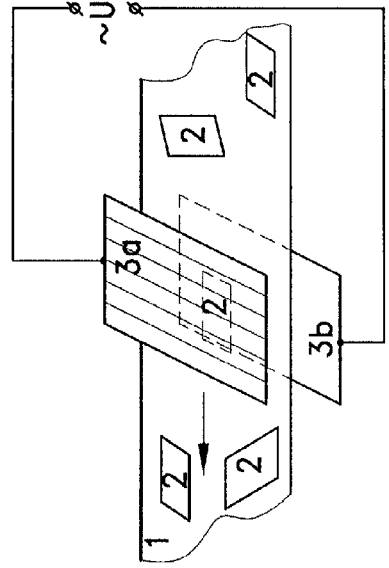
Figure 1C:
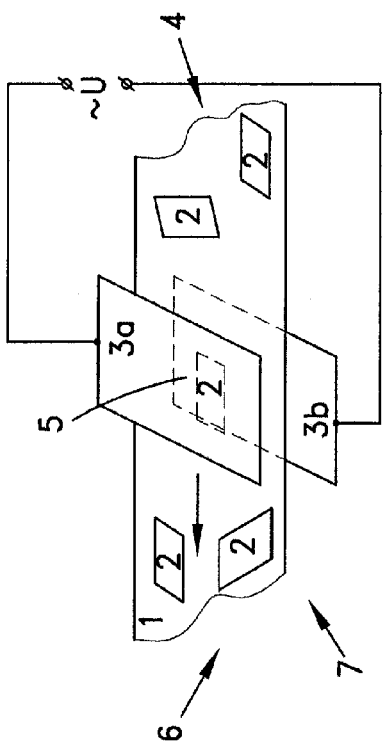
Figure 1D:
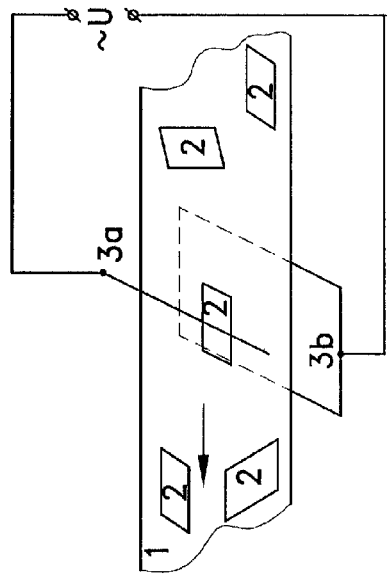
Figure 2:
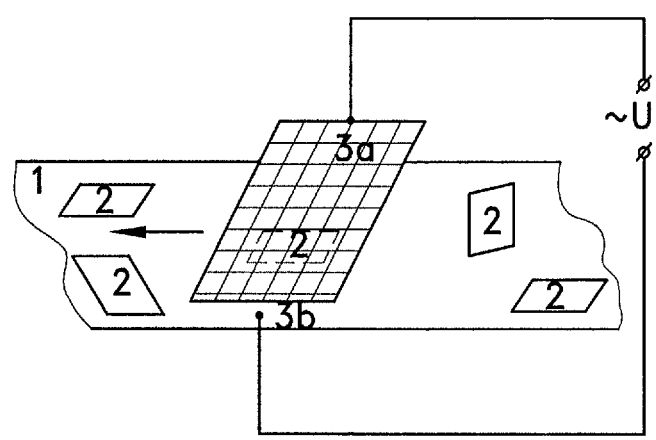

Priority is claimed as a continuation-in-part of international application number PCT/IL2011/000109, filed on Jan. 31, 2011; which claims priority to Israeli Patent application number 203741, filed on Feb. 4, 2010.

FIELD OF THE INVENTION

The present invention relates to the modification of particle size in powders, particularly powders in a closed item, comprising the exposure of said powder to external electric field and producing either a bunching effect or coulombic explosion, which either increases or decreases the aggregate size.

BACKGROUND OF THE INVENTION

Postal and delivery services were used in the 2001 bioterrorist attacks as a conduit to disperse and release anthrax across the United States. Letters containing a dried form of *Bacillus anthracis* spores were mailed through the U.S. Postal Service to several news media offices and two Democratic U.S. Senators. Several postal agents were directly in contact with the anthrax spores when handling the closed mail pieces. When the letters were opened, the volatile powder was dispersed and the spores inhaled. In the following months, five people died from anthrax spores inhalation and a total of eighteen others contracted some form of the disease. This event caused a panic wave in the population: several hundred thousands of people took broad-spectrum antibiotics, and even more purchased antibiotics for prophylaxis.

As bad as the anthrax attacks were, an outbreak of a biologically engineered pathogen dispersed by the mailing system would have been potentially more devastating. According to some biodefense specialists, the "senate" anthrax can be considered as a perfect example of a "bioweaponized" agent, as highly pure dried spores were successfully converted into an advanced aerosol. The processes of production of a bioweapon are technically complex. Inhalable microparticles have to be of a specific size range, typically one to five micrometers: particles smaller than one micrometer behave as a gas and are inhaled and exhaled from the respiratory system whereas particles of more than five micrometers are too large to stay airborne for a long time. Untreated anthrax spores, which are few micrometers in size, when introduced into an envelope and being subjected to mechanical contact with one another, tend to clump in large clusters due to adhesive properties of their surface. A specific treatment (aerosolization, weaponization) is performed to keep them dispersed and ensure that they have a proper size to be airborne for a long time.

Nowadays, suspicious mail pieces are neutralized by means of various types of irradiation or chemical procedures. U.S. Pat. No. 6,660,227 relates, for example, to a device in which mail pieces are isolated, analyzed and further exposed to ultraviolet irradiation. Among the main problems of such systems is that UV irradiation can only be used for sterilizing the external side of the mail pieces, as light emitted in this region of the spectrum does not penetrate the paper. U.S. Pat. No. 6,737,029 relates to a system for sterilizing mail articles by introducing them into a confined chamber which is filled with ozone to a degree that guarantees ozonization of all organic compounds, including viral nucleic acids and bacteria. Although this system is efficient for sterilizing the interior of the mail piece, the process is slow and expensive, energy consuming, and requires specifically trained staff to operate. Moreover, treatment of residual ozone used during sterilization is critical as small amounts of this gas are carcinogenic for humans.

Sterilization of all the circulating mail to eliminate the risk of a terrorist attack seems to be unachievable as it would be time-consuming, energy-consuming, and highly expensive. Therefore, modern strategies tend to direct their effort to thwart the volatility of the harmful microsized agents. WO 03/057260 relates, for example, to a method for reducing "volitation" of airborne biological agents while processing mail, using an apparatus that confers a charge to the microparticles in a special pre-charging chamber. Once charged, the particles which are located out of envelopes are attracted by an electric field by means of coulombic forces and are precipitated onto a surface having an opposite charge. The mails are then further processed for analysis and sterilization. This method and the described apparatus are well known in the field of air cleaning as electrostatic precipitator (ESP). However, for use in reducing powder volatility, ESP has several disadvantages:

efficiency of ESP is high only under special conditions—geometry of DC field and undisturbed air flow—which definitely cannot be met for the transporter carrying envelopes and other mailed objects of arbitrary positions and dimensions. Correspondingly, this method can not fulfill its main goal—to eliminate volatility of dangerous particles which came out of their envelopes due to their imperfect isolation.

said charging induces a repulsive effect between the particles, and also between the particles and envelopes, effectively increasing the volatility of non-captured particles.

method is time consuming because a lengthy time exposure is required to ensure that all the particles are charged;

electric field has to be constantly maintained throughout the mail transportation to the sterilization chamber in order to avoid particles spreading;

There is therefore a need for a method and an apparatus capable of neutralizing potentially harmful powders enclosed in mails, which overcome the disadvantages of the prior art.

It is therefore an object of the present invention to provide a fast and effective method for neutralizing harmful powders in mail by reducing the volatility of microparticles.

It is another object of the present invention to provide a method for the detection and characterization of harmful powders in mails.

It is a further object of the present invention to provide a method for the deactivation of harmful powders in mails.

It is yet a further object of the present invention to provide an apparatus for the neutralization of harmful powders in mails, and optionally their identification and deactivation.

Other objects and advantages of the present invention will appear as the description proceeds.

SUMMARY OF THE INVENTION

The invention provides a method for fast modification of particle size of powder in a closed item, comprising the exposure of said powder to external electric field producing a bunching effect on the particles composing said powder or effect of disintegration of particles clusters, thereby changing the particle size distribution of said powder. Said bunching effect may be caused by a low frequency electric field, frequency being less than or of the order of $10^2$ Hz, with an amplitude which is lower than the level of a corona discharge, typically smaller than $10^4$ V/cm. Said bunching effect may be caused by a high frequency alternating electric field, frequency being typically higher than $10^3$ Hz, wherein said electric field has an amplitude approaching or exceeding the level of a corona discharge, and wherein said field has a period of alternations much smaller than the typical time of attaining electric charge by said micro-particles. The preferred method according to the invention does not need the particles to be charged. Said electric field in the method of the invention does not confer a significant charge to said particles, and said bunching effect lasts long after said exposure. Said electric field may have an antimicrobial effect, essentially sterilizing said exposed item. Said antimicrobial effect may be caused by the generation of ozone. Said antimicrobial effect may, in other embodiment, be caused by the generation of ultraviolet light. In a preferred embodiment of the method according to the invention, the final characteristics of said electric field are reached by gradually increasing its frequency and/or amplitude. The values of frequency and amplitude causing the bunching effect may be determined via a detecting device. In an important aspect of the invention, said bunching effect can be reversed by applying an electric field with low frequency, being lower than or of the order of $10^2$ Hz, and high amplitude, being higher than or of the order of $10^4$ V/cm, causing the disintegration of particles clusters ("bunches", agglomerates), the coulombic explosion being one of the physical mechanisms, leading to this disintegration. The method has no negative impact on the item.

The invention provides an apparatus for processing items containing enclosed powder, comprising means for generating a preferably non-uniform electric field, wherein said electric field is used to modify the particle size of said powder enclosed in said item, and wherein said field induces a bunching effect on said particles or disintegration of aggregates.

In a preferred embodiment, the method according to the invention for fast modification of particle size of powder in a closed item, comprises the exposure of said powder to external electric field producing a bunching effect on the particles composing said powder, wherein said powder is a food product and said bunching effect results in dry agglomeration of said food powder.

In other preferred embodiment, the method according to the invention for fast modification of particle size of powder in a closed item, comprises the exposure of said powder to external electric field producing a bunching effect on the particles composing said powder, wherein said powder is a pharmaceutical product and said bunching effect results in dry agglomeration of said pharmaceutical powder.

In still another preferred embodiment, the method according to the invention for fast modification of particle size of powder in a closed item, comprises the exposure of said powder to external electric field producing coulombic explosion of the aggregated particles composing said powder, wherein said powder is a pharmaceutical product and said coulombic explosion results in lowering the particle size of said pharmaceutical powder. In one embodiment, the initial particles size distribution is restored and undesired agglomerates are disintegrated by applying an electric field with low frequency, being lower than or of the order of $10^2$ Hz, and high amplitude, being higher than or of the order of $10^4$ V/cm, causing a coulombic explosion.

The invention relates to an apparatus for processing items containing enclosed powder, wherein said powder comprises food product or pharmaceutical product, comprising means for generating a preferably non-uniform electric field, wherein said electric field induces a prolonged bunching effect on the particles or disintegration of particles clusters (agglomerates) of said powder, and results in aggregation or deagglomeration of the initial powder. In another embodiment, the apparatus according to the invention comprises means for generating a preferably non-uniform electric field, wherein said electric field is used for dry agglomeration of powder within the packages or for restoring the initial large size of agglomerates, without re-packaging said powder product.

The invention provides, in a preferred embodiment, a method for fast modification of particle size of powder in a closed item, comprising the exposure of said powder to external electric field producing a bunching effect on the particles composing said powder, thereby annihilating volatility of said powder wherein said powder is a volatile harmful powder enclosed in mail items. Said particles are preferably microparticles. Said method does not require preliminary detection of said powder. Said mail items are preferably envelopes or other closed mail pieces. Said microparticles may be of chemical and/or biological origin. Said bunching effect is preferably carried out within an area limited by the size of said mail item, within a limited time interval, without need for applying electric field or other means after attaining said bunching effect, for maintaining the powder in the bunched condition. Said bunching effect may be used for improving the efficiency of matter-detecting devices. Said matter-detecting devices may be based on a terahertz radiation. Said matter detecting devices may be based on a visible light radiation. Said changing frequency and amplitude values may be used to identify the material enclosed in said item which is a mail item.

The invention is directed to an apparatus for processing mail items, comprising means for generating a preferably non-uniform electric field, wherein said electric field is used to neutralize volatile microparticles enclosed into said processed mail item, and wherein said field induces a prolonged bunching effect on said microparticles. Said prolonged bunching effect preferably occurs in a small area, limited only by a typical size of the enclosure of said mail items, this property making the apparatus very compact. Provided is a system comprising the above apparatus, a computer, a display screen, a dedicated software, and a material-detecting device enabling neutralization, detection, identification, or deactivation of harmful powders in mail items.

Another aspect of the present invention relates to a method for fast neutralization of volatile harmful powders enclosed in mail items, which comprises the brief (of the order of 1 second or less) exposure of said mail items to an external electric field producing a prolonged bunching effect on the microparticles composing the powder enclosed in or deposited on the envelope, thereby annihilating their volatility. The bunching effect, caused by polarization of particles' material, lasts enough time after application of the electric field to enable processing the mail items, including performing all necessary analyses and operations. The method disclosed inhere does not require preliminary detection of said powder and has no negative impact on the processed mail item. The method is applicable to all kinds of mail items, such as envelopes or any other closed mail pieces. Harmful powders which are neutralized by the present invention may be composed of microparticles of chemical and/or biological origin. The particles may comprise inorganic or organic matter, or they may comprise biological entities.

This bunching effect is provided by polarization of the particles' material and takes place on electrically neutral or only weakly charged particles, because same-charge particles repel one another due to the coulombic repulsion. Correspondingly, charging of particles is not necessary, rather it has to be avoided. In one embodiment of the method of the invention, the bunching effect is caused by a low frequency electric field (frequency is less or of the order of $10^2$ Hz), with an amplitude which is kept lower than the level of a corona discharge (typically smaller than $10^4$ V/cm) in order to prevent particles charging. In another embodiment of the method of the invention, the bunching effect is caused by a high frequency electric field (frequency typically higher than $10^3$ Hz), wherein the amplitude of electric field may approach or even exceed the level of a corona discharge, but the period of alternations, corresponding to the high frequency, is much smaller than t, where t is a typical time of attaining the charge by a micro-particle (see: W. C. Hinds, Aerosol Technology: Properties, Behavior, and Measurement of Airborne Particles, $2^{nd}$ edition, Wiley-Interscience, 1999). The method according to the invention may achieve said bunching effect without charging said microparticles, or without conferring a significant charge to said microparticles by said electric field. The instant method does not need microparticles to be charged.

Said bunching effect immobilizes said powder and confines it in the volume enclosed by said mail item, such as envelope or package. The method according to the invention attains said bunching effect, and the apparatus according to the invention carries out said bunching effect, within an area limited by the size of said mail item, and also within a limited time interval, as described herein, without need for applying electric field or other means after attaining said bunching effect for maintaining the powder in the bunched condition.

The final characteristics of the electric field are preferably reached by gradual increase of its frequency and/or amplitude. In one embodiment of the invention, the values of frequency and amplitude causing the bunching effect are determined with a detecting device and are used to identify the material enclosed in the mail item.

In a further embodiment of the invention, the method disclosed inhere induces a bunching effect which is used for improving the efficiency of matter detecting devices, such as devices based on terahertz radiations or visible light radiations.

In still a further embodiment of the method of the invention, the applied electric field has an antimicrobial effect, which essentially sterilizes the exposed mail item. This antimicrobial effect may be obtained, for example, through the generation of ozone or ultraviolet by an electric field.

In still a further embodiment of the invention, the disclosed method enables to revert the bunching effect by applying an electric field with low frequency (smaller or of the order of $10^2$ Hz) and high amplitude (higher or of the order of $10^4$ V/cm), hence causing particles charging, followed by disintegration of the bunches and other aggregated particles clusters, due to mutual coulombic repulsion of individual microparticles. Further in the text this process of disintegration is referred as "coulombic explosion" for briefness and uniformity.

Said electric field in the method according to the invention aggregates the particles of a fine powder to bigger clods, essentially without conferring a charge to said particles, whereas the bunching effect lasts enough long after said exposure.

In yet another aspect of the invention, disclosed is an apparatus for processing mail items, comprising means for generating a preferably non-uniform electric field, wherein said electric field is used to neutralize volatile microparticles enclosed into said processed mail item, and wherein said field induces a prolonged bunching effect of said microparticles. Said prolonged bunching effect occurs in a small area limited only by a typical size of the mail enclosure, this property making the apparatus very compact.

In a further aspect of the invention, disclosed is a system comprising an apparatus as above-described, a computer, a display screen, a dedicated software, and a material-detecting device for the neutralization, detection, identification and deactivation of harmful powders in mail items.

BRIEF DESCRIPTION OF THE DRAWINGS

The above and other characteristics and advantages of the invention will be more readily apparent through the following examples, and with reference to the appended drawings, wherein:

FIG. 1. schematically shows several embodiments of the apparatus of the invention comprising one upper electrode and one lower electrode, the electrodes comprising shapes of plates in FIG. 1A, grids in FIG. 1B, single wire in FIG. 1C, and parallel wires in FIG. 1D; and FIG. 2. schematically represents another embodiment of the apparatus of the invention comprising one upper electrode and a conductive transporter.

DETAILED DESCRIPTION OF THE INVENTION

It has now been found that the particle size distribution of powders, or of powders in closed items, may be modified by applying electric field in a special way. Said powder or said closed item is exposed to external electric field which produces a bunching effect on the particles or a disintegration effect on particle clusters, thereby changing the particle size distribution of said powder.

The present invention provides a method and apparatus for the effective neutralization, identification and deactivation of active volatile inhalable powders in mails. The present invention is used for a fast, routine and effective treatment of closed mails, in particular envelopes, and drastically decreases the risks of contamination by any chemical or biological airborne agent. It was found by the inventor that exposing mails enclosing microsized particles to a particular electric field, induces a prolonged bunching effect of said particles, and as a result neutralizes their volatility. This prolonged bunching effect was observed by the inventor even after removing the electric field. The application of the electric field neutralizes both the microparticles enclosed in the mail and the particles that may be prevalent outside said mail. Therefore, after using the present invention, safe handling of the mail pieces is enabled without any risk of inhalation of harmful particles. The present invention presents several other advantages: it improves the detection efficiency of suspect powders in closed mails, enables their characterization and their deactivation. The present invention can also be employed to reverse the bunching effect applied to the microparticles. It may be of particular interest if laboratory analysis of suspect powdered material is needed: safe sampling can be performed of the powder aggregate, and by canceling the bunching effect, the analysis of the individual particles size and shape is enabled.

The method of the invention ensures fast neutralization of aerosolized powder in closed mails by the application of electric field inducing a bunching effect of the microparticles. This phenomenon does not comprise conferring a charge to the microparticles which remain neutral. Without wishing to be limited by any particular theory, the inventor believes that the very efficient performance of the novel method and device has to be attributed to the dominating role of polarization phenomena on microparticles motion in electric fields of certain parameters. The strength of the resulting forces depends on the medium, the electrical properties, shape and size of the particles, as well as on the characteristics of the applied electric field, such as the shape of the field gradient, the amplitude and the frequency. Consequently, given the amplitude and shape, fields of a particular frequency can manipulate particles with great selectivity. In the present invention, the electrical field is generated either in a high frequency mode or in a low frequency mode, each of those being suitable for polarizing the microparticles and inducing the bunching effect. The parameters of electric field in each mode are chosen in a manner, which prevents significant particles charging. In the high frequency mode (frequency higher than or of the order of $10^3$ Hz), the electric field may be applied with high amplitude, approaching or even exceeding the level of a corona discharge (typically higher than or of the order of $10^4$ V/cm), but the period of alternations (T), corresponding to high frequency (f), is much smaller than t, where t corresponds to the typical time of a micro-particle charging—thus avoiding the particles to be strongly charged. In the low frequency mode (frequency smaller or of the order of $10^2$ Hz), the electric field with a low amplitude has to be applied, which is much lower than the level of a corona discharge (typically lower than $10^4$ V/cm), hence avoiding particles charging. Among the other characteristics of the field that may vary are its shape (according to the shape of the electrodes), the type of the electric signal (sinusoidal, rectangular, etc.), and its pulse ratio.

In both modes, the effect of neutralization of powders volatility in mail pieces requires the electric field to be applied to objects only for a very short time durations, typically 0.1 to 1 sec.

In FIG. 1, several embodiments of the apparatus of the invention are shown. The apparatus 7 comprises a transporter belt 1 made of non-conductive material, on which the mail pieces 2 are disposed, said transporter 1 moving the mail pieces 2 from the front side 4 of the apparatus towards the neutralization zone 5 and to the back side 6 of the apparatus. The neutralization zone 5 comprises an upper electrode 3*a* and a lower electrode 3*b* placed parallel to the transporter plane, wherein said electrodes interact to generate a preferably non-uniform electric field. The electric field is directed approximately perpendicularly to the transporter plane. The upper electrode 3*a* and the lower electrode 3*b* may have various shapes such as a plate, a grid, a single wire, parallel wires, etc., depending on concrete application modes (in the case of plate electrode the bunching effect is still provided by local non-uniformities of the field, created by individual microparticles). In some embodiments of the invention, the transporter 1 is made of a conductive material and replaces the lower electrode 3*b* (FIG. 2). In yet another embodiment of the apparatus of the invention, the transporter moves the mail pieces in a continuous motion (preferably about 10 cm/s) on an approximately one meter width plane. In this embodiment, a deactivation rate of few hundreds mail pieces per minute can be achieved. In another embodiment of the apparatus of the invention, the motion of the transporter is not continuous, as it may be interrupted to enable longer exposure of large transporter areas to the electric field, or when further analysis or deactivation of the powder contained in the mail piece is required. In some embodiments of the invention, the apparatus comprises an additional system for identifying the type of the powder enclosed in the treated mail and its deactivation. Such a system preferentially comprises a computer, a display screen, a dedicated software and a detection apparatus.

The bunching of the microparticles can be used to improve the efficiency of current detection methods. Methods known in the art for the detection of matter rely on the emission of specific radiations in the direction of the sample of interest and the registration of the resulting radiation after their interaction with said sample (scattering, absorption, transmission or emission, etc.). However, detection methods are always limited by the size and the amount of particles that can be detected. In the particular case of detection of powders in closed mails, the limiting factor is the low volumetric concentration of the powdered material. As the present invention enables the bunching of the particles, it helps increasing the volumetric density of the material by several orders of magnitude, with corresponding improvement of the detection efficiency. Detectors are capable to effectively detect particles of a dispersed material (material consisting of small particles) when they use radiations with a wavelength which is much smaller than or at least of the order of size of particles of said material. In the present case, visible light (0.4-0.8 μm) or terahertz radiations (0.1-1 mm) can be used after the bunching of the particles, which form objects (bunches) of about 0.1-1 mm in size. This feature of the invention is of a particular interest as many biologically or chemically active aerosols are extremely harmful when used in very small amounts, and may be therefore undetectable by conventional detectors. Terahertz radiation may be preferably used as it penetrates efficiently the paper and becomes much more effective for detection of formation of bunches with size, comparable with its wavelength. The use of a powerful visible light source also becomes conceivable for detection of bunches formation. Therefore, some embodiments of the present invention include detecting systems which enable the detection and the visualization of clusterized microparticles.

The present invention also provides a method for the identification of the powdered material contained in mail items. As described before, the bunching of the microparticles is due to electronic forces resulting from the application of an electric field. The threshold parameters of the field, e.g., amplitude and frequency, at which the beginning of the bunching effect is observed, may be used for identifying the powdered agent. Indeed, these parameters are directly related to the unique dielectric constant of the material by the Klaudio-Mazotti equation (see: Herbert A. Pohl, "Dielectrophoresis, The behavior of neutral matter in non-uniform electric fields", Cambridge University Press, London, 1978). Therefore, in some embodiments of the invention, the transporter brings into the electric field a mail piece which should be exposed. For a given geometry and frequency, the field strength has to be preliminarily calibrated for different materials. For a given fixed frequency, the field amplitude is gradually raised from a minimum value (preferably 0) and if and when an aggregation is observed (either under visible light or by THz irradiation, or by any another relevant detecting system), the field parameters (in this example—amplitude) are stored and compared to a pre-registered database for the identification of the material in real-time. The beginning of the bunching effect can be observed by a trained person or assisted by a computer with machine vision software.

The electric field as produced by the apparatus of the invention can also be used to sterilize the mail piece. Ultraviolet radiation and ozone are known to have destructing effects on biological entities and are commonly used for deactivation of powders of biological origin. Adjusting the parameters of the electric field generated by the apparatus of the invention (preferably at low frequency and high amplitude), enables the creation of the favorable conditions for initiation of a corona discharge near mail peaces and in the closed mail pieces due to local electric field gradients created by the enclosed particles. These conditions (corona discharge) are known to be followed by generation of UV radiation and ozone. As a result, a very high concentration of sterilizing factors (UV, ozone) is provided in very close proximity to each particle and is used to deactivate them in a very short period of time. An electrode having preferably the shape of a grid, or comprising a plurality of parallel conductive wires, or a plate can be used. The electrode area may be large enough to deactivate many mail pieces at a time. In one embodiment of the apparatus of the invention, the sterilization stage is performed following the two preceding steps, i.e., neutralization and identification, at the same position on the transporter, and by changing the parameters of the electric field. The time for the third step (sterilization) is from several minutes up to about one hour.

The method of the present invention also allows the recovery of the original particles' size by reversing the bunching effect. It was found by the inventor that applying specific field parameters (low frequency $f \ll 10^2$ Hz and high amplitude ($\geq 10^4$ V/cm), onto the microparticles clusters induces the complete separation of bunches and clusters to original individual microparticles. This procedure can be used when single particles should be studied, e.g., for laboratory analysis.

The method according to the invention may be employed for increasing or decreasing the degree of particle agglomeration. When employing the method for processing powders in flat objects, for example when neutralizing volatile powders in envelopes, practically 2D (two dimensional) system is used. When using the method for larger items, like for dry agglomeration (dry granulation) of powders in food industry, rather spatial (3D) type of the method is employed; realized, for example, by a structure (3D grid) of thin-wire collecting electrodes (with typical spatial separation of the order of cm) placed in the volume. The initial powder to be agglomerated is blown throw the grid of collecting electrodes, in one or more cycles. The agglomerated material can be periodically shaken off the grid into the collecting receptacle. This agglomeration procedure may be used either separately or as one of the stages in a technological chain, together with other methods, for improving the final quality of the resulting product. For example, it is known, that an important disadvantage of the "spray drying" granulation process in the instant coffee production is the too small resulting size of particles (smaller than 300 micron). The addition of our apparatus, which is capable to increase the size of agglomerates in controllable manner through the parameters of electric field will definitely compensate this disadvantage.

In another aspect, the invention may be employed for adjusting the state of powder products, like instant coffee, within closed paper packages (usually flat). In one embodiment, the particle size of the product is finalized by means of the method according to the invention. In another embodiment, the method enables to restore the particle size after unwanted change of consistency, like after crushing the packets, even without repacking the product.

In another aspect, the dry agglomeration according to the invention may be employed in processing pharmaceutical powder products. In one embodiment, the particle size of a pharmaceutical product is increased, so decreasing unwanted volatility. In other embodiment, two big aggregates may be dispersed into more volatile powders, when necessary, by employing coulombic explosion according to the instant process; this may, for example, restore the initial size distribution of particles in the case of undesired aggregation, which may happen spontaneously during storage of powders. The instant procedure can thus save powders for inhalation, which would otherwise be unusable for low volatility. The instant method may be used for adjusting the shape and sizes of the particles in aerosol preparations (usually smaller than 1-2 microns, approximately spherical shape).

Although embodiments of the invention have been described by way of illustration, it will be understood that the invention may be carried out with many variations, modifications, and adaptations, without exceeding the scope of the claims.

The invention claimed is:

1. A method for fast modification of particle size of powder in a closed item, comprising the exposure of said powder to an external electric field producing a bunching effect, thereby changing the particle size distribution of said powder;
   wherein the final characteristics of said electric field are reached by gradually increasing its frequency and/or amplitude;
   wherein the beginning of the bunching effect is observed either under visible light or by THz irradiation, or by any another relevant detecting system, the amplitude and frequency are stored and compared to a pre-registered database for the identification of the material in real-time.

2. The method according to claim 1, wherein said bunching effect is caused by a low frequency electric field, frequency being less than or of the order of $10^2$ Hz, with an amplitude which is lower than the level of a corona discharge, typically smaller than $10^4$ V/cm.

3. The method according to claim 1, wherein said bunching effect is caused by a high frequency alternating electric field, frequency being typically higher than $10^3$ Hz, wherein said electric field has an amplitude approaching or exceeding the level of a corona discharge, and wherein said field has a period of alternations much smaller than the typical time of attaining electric charge by said micro-particles.

4. The method according to claim 1, which does not need the particles to be charged.

5. The method according to claim 1, wherein said electric field does not confer a significant charge to said particles.

6. The method according to claim 1, wherein said bunching effect lasts long after said exposure.

7. The method according to claim 1, wherein said electric field has an antimicrobial effect, essentially sterilizing said exposed item.

8. The method according to claim 7, wherein said antimicrobial effect is caused by the generation of ozone.

9. The method according to claim 7, wherein said antimicrobial effect is caused by the generation of ultraviolet light.

10. A method according to claim 1, wherein the final characteristics of said electric field are reached by gradually increasing its frequency and/or amplitude.

11. A method according to claim 10, wherein the values of frequency and amplitude causing the bunching effect are determined via a detecting device.

12. The method according to claim 10, wherein said bunching effect can be reversed by applying an electric field with low frequency, being lower than or of the order of $10^2$ Hz, and high amplitude, being higher than or of the order of $10^4$ V/cm, causing a coulombic explosion.

13. The method according to claim 1, wherein said method has no negative impact on the item.

14. The method according to claim 1 for fast modification of particle size of powder in a closed item, comprising the exposure of said powder to external electric field producing a bunching effect on the particles composing said powder, wherein said powder is a food product and said bunching effect results in dry agglomeration of said food powder.

15. The method according to claim 1 for fast modification of particle size of powder in a closed item, comprising the exposure of said powder to external electric field producing a bunching effect on the particles composing said powder, wherein said powder is a pharmaceutical product and said bunching effect results in dry agglomeration of said pharmaceutical powder.

16. The method according to claim 1 for fast modification of particle size of powder in a closed item, comprising the exposure of said powder to external electric field producing a bunching effect on the particles composing said powder, thereby annihilating volatility of said powder wherein said powder is a volatile harmful powder enclosed in mail items.

17. The method according to claim 1, wherein said method does not require preliminary detection of said powder.

18. The method according to claim 1, wherein said mail items are envelopes or other closed mail pieces.

19. The method according to claim 1, wherein said particles are of chemical and/or biological origin.

20. The method according to claim 1, wherein said bunching effect is carried out within an area limited by the size of said mail item, within a limited time interval, without need for applying electric field or other means after attaining said bunching effect, for maintaining the powder in the bunched condition.

21. The method according to claim 1, wherein said bunching effect is used for improving the efficiency of matter-detecting devices.

22. The method according to claim 21, wherein said matter-detecting devices are based on a terahertz radiation.

23. The method according to claim 21, wherein said matter detecting devices are based on a visible light radiation.

24. The method according to claim 1, wherein said frequency and amplitude values are used to identify the material enclosed in said item which is a mail item.

* * * * *